US00PP30396P2

(12) United States Plant Patent
Yamada

(10) Patent No.: US PP30,396 P2
(45) Date of Patent: Apr. 16, 2019

(54) ***PETUNIA* PLANT NAMED 'SUNPETU 211'**

(50) Latin Name: ***Petunia* x *hybrida***
Varietal Denomination: Sunpetu 211

(71) Applicant: Masahiro Yamada, Shiga (JP)

(72) Inventor: Masahiro Yamada, Shiga (JP)

(73) Assignee: Suntory Flowers Limited, Tokyo (JP)

( * ) Notice: Subject to any disclaimer, the term of this patent is extended or adjusted under 35 U.S.C. 154(b) by 0 days.

(21) Appl. No.: 15/732,934

(22) Filed: Jan. 12, 2018

(51) Int. Cl.
*A01H 5/02* (2018.01)

(52) U.S. Cl.
USPC ..... Plt./356.13

(58) Field of Classification Search
USPC ..... Plt./356.13
CPC ..... A01H 5/02; A01H 5/00; A01H 6/824
See application file for complete search history.

*Primary Examiner* — June Hwu
(74) *Attorney, Agent, or Firm* — C. A. Whealy

(57) ABSTRACT

A new and distinct cultivar of *Petunia* plant named 'Sunpetu 211', characterized by its upright and mounding plant habit; vigorous growth habit; freely branching habit; freely flowering habit; long flowering period; large flowers that are bright purple with a white-colored star pattern; and good garden performance.

1 Drawing Sheet

Botanical designation: *Petunia* x *hybrida*.
Cultivar denomination: 'SUNPETU 211'.

BACKGROUND OF THE INVENTION

The present invention relates to a new and distinct cultivar of *Petunia* plant, botanically known as *Petunia* x *hybrida* and hereinafter referred to by the name 'Sunpetu 211'.

The new *Petunia* plant is a product of a planned breeding program conducted by the Inventor in Higashiomi, Shiga, Japan. The objective of the breeding program is to create new upright, mounding and freely-flowering *Petunia* plants with attractive flower colors and patterns.

The new *Petunia* plant originated from a cross-pollination made by the Inventor in July, 2014 in Higashiomi, Shiga, Japan of a proprietary selection of *Petunia* x *hybrida* identified as code designation SA8294, not patented, as the female, or seed, parent with a proprietary selection of *Petunia* x *hybrida* identified as code designation PSRS, not patented, as the male, or pollen, parent. The new *Petunia* plant was discovered and selected by the Inventor as a single flowering plant within the progeny of the stated cross-pollination in a controlled greenhouse environment in Higashiomi, Shiga, Japan in July, 2015.

Asexual reproduction of the new *Petunia* plant by terminal vegetative cuttings in a controlled greenhouse environment in Higashiomi, Shiga, Japan since January, 2016 has shown that the unique features of this new *Petunia* plant are stable and reproduced true to type in successive generations.

SUMMARY OF THE INVENTION

Plants of the new *Petunia* have not been observed under all possible combinations of environmental conditions and cultural conditions. The phenotype may vary somewhat with variations in environmental conditions such as temperature and light intensity without, however, any variance in genotype.

The following traits have been repeatedly observed and are determined to be the unique characteristics of 'Sunpetu 211'. These characteristics in combination distinguish 'Sunpetu 211' as a new and distinct *Petunia* plant:

1. Upright and mounding plant habit.
2. Vigorous growth habit.
3. Freely branching habit.
4. Freely flowering habit.
5. Long flowering period.
6. Large flowers that are bright purple with a white-colored star pattern.
7. Good garden performance.

Plants of the new *Petunia* can be compared to plants of the female parent selection. Plants of the new *Petunia* differ primarily from plants of the female parent selection in flower color as plants of the female parent selection have violet-colored flowers with a white-colored star pattern. In addition, flowers of plants of the new *Petunia* are larger than flowers of plants of the female parent selection.

Plants of the new *Petunia* can be compared to plants of the male parent selection. Plants of the new *Petunia* differ primarily from plants of the male parent selection in flower color as plants of the male parent selection have rose pink-colored flowers with a white-colored star pattern.

Plants of the new *Petunia* can also be compared to plants of the *Petunia* hybrid 'PBLRS38-0', disclosed in U.S. Plant Pat. No. 25,265. In side-by-side comparisons, plants of the new *Petunia* and 'PBLRS38-0' differ primarily in the following characteristics:

1. Plants of the new *Petunia* are more upright than and not as outwardly spreading as plants of 'PBLRS38-0'.
2. Plants of the new *Petunia* are taller than and not as broad as plants of 'PBLRS38-0'.
3. Plants of the new *Petunia* have larger leaves than plants of 'PBLRS38-0'.
4. Plants of the new *Petunia* are more freely flowering than plants of 'PBLRS38-0'.
5. Plants of the new *Petunia* have larger flowers than plants of 'PBLRS38-0'.

BRIEF DESCRIPTION OF THE PHOTOGRAPHS

The accompanying colored photographs illustrate the overall appearance of the new *Petunia* plant showing the colors as true as it is reasonably possible to obtain in colored reproductions of this type. Colors in the photographs may differ slightly from the color values cited in the detailed botanical description which accurately describe the colors of the new *Petunia* plant.

The photograph at the top of the sheet comprises a side perspective view of a typical flowering plant of 'Sunpetu 211' grown in a container.

The photograph at the bottom of the sheet is a close-up view of a typical flowering plant of 'Sunpetu 211'.

DETAILED BOTANICAL DESCRIPTION

The aforementioned photographs and following observations, measurements and values describe plants grown during the summer in 20-cm containers in an outdoor nursery in Higashiomi, Shiga, Japan and under cultural practices typical of commercial *Petunia* production. During the production of the plants, day temperatures averaged 23° C. and night temperatures averaged 13° C. Plants were six and seven months old when the photographs and description, respectively, were taken. In the following description, color references are made to The Royal Horticultural Society Colour Chart, 2015 Edition, except where general terms of ordinary dictionary significance are used.

Botanical classification: *Petunia* x *hybrida* 'Sunpetu 211'.

Parentage:

*Female, or seed, parent*.—Proprietary selection of *Petunia* x *hybrida* identified as code designation SA8294, not patented.

*Male, or pollen, parent*.—Proprietary selection of *Petunia* x *hybrida* identified as code designation PSRS, not patented.

Propagation:

*Type*.—By terminal vegetative cuttings.

*Time to initiate roots, summer and winter*.—About one week at temperatures about 15° C. to 20° C.

*Time to produce a rooted young plant, summer and winter*.—About three weeks at temperatures about 15° C. to 20° C.

*Root description*.—Fibrous; typically white in color, actual color of the roots is dependent on substrate composition, water quality, fertilizer type and formulation, substrate temperature and physiological age of roots.

*Rooting habit*.—Freely branching; dense.

Plant description:

*Plant form and growth habit*.—Upright and mounding plant habit; freely branching habit with numerous lateral branches developing per plant; pinching enhances lateral branch development; vigorous growth habit.

*Plant height*.—About 30 cm.

*Plant diameter*.—About 56 cm.

Lateral branch description:

*Length*.—About 26 cm.

*Diameter*.—About 2.3 mm.

*Internode length*.—About 2.1 cm.

*Strength*.—Strong, flexible.

*Aspect*.—Upright to outwardly.

*Texture*.—Pubescent, rough.

*Color*.—Close to 145A.

Leaf description:

*Quantity and arrangement*.—About 16 leaves per lateral branch; alternate, simple.

*Length*.—About 4.6 cm.

*Width*.—About 2.7 cm.

*Shape*.—Elliptical.

*Apex*.—Narrowly acute.

*Base*.—Attenuate.

*Margin*.—Entire.

*Texture, upper and lower surfaces*.—Pubescent, rough.

*Venation pattern*.—Pinnate; reticulate.

*Color*.—Developing leaves, upper surface: Close to NN137C. Developing leaves, lower surface: Close to 137C. Fully expanded leaves, upper surface: Close to 137B; venation, close to 145B. Fully expanded leaves, lower surface: Close to 147B; venation, close to 145C.

*Petioles*.—Length: About 6.1 mm. Diameter: About 3.1 mm. Texture, upper and lower surfaces: Pubescent, rough. Color, upper and lower surfaces: Close to 145B.

Flower description:

*Flower arrangement and habit*.—Large single-type salverform flowers arising from upper leaf axils; freely flowering habit with usually about three to five flowers developing per lateral branch and about 150 flowers developing per plant during the flowering season; flowers face mostly upright to outwardly.

*Fragrance*.—None detected.

*Natural flowering season*.—Early flowering habit; plants of the new *Petunia* initiate and develop flowers about three to four weeks after planting; long flowering period, flowering commences naturally during the spring and plants flower continuously throughout the summer until late autumn in Japan.

*Flower longevity*.—Individual flowers last about seven to ten days on the plant; flowers not persistent.

*Flower buds*.—Length: About 4 cm. Diameter: About 1.5 mm. Shape: Cylindrical. Color: Close to 145D with stripes, close to 83D; developing petals, close to 83A.

*Flower diameter*.—About 6.5 cm.

*Flower tube length*.—About 2.6 cm.

*Flower tube diameter, proximally*.—About 2.4 mm.

*Flower tube diameter, distally*.—About 9 mm.

*Corolla*.—Quantity and arrangement: Five in a single whorl, fused at the base and opening into a flared trumpet. Petal length from throat: About 2 cm. Petal width: About 2.5 cm. Petal shape: Roughly spatulate. Petal apex: Cuspidate. Petal margin: Entire; slightly lobed; undulate. Petal texture, upper and lower surfaces: Smooth, glabrous; velvety. Throat texture: Smooth, glabrous. Tube texture: Pubescent. Color: Petal, when opening, upper surface: Main color, darker than N78A; star pattern, close to NN155B. Petal, when opening, lower surface: Main color, close to N80B; star pattern, close to 157D. Petal, fully opened, upper surface: Main color, close to between N78A and NN78A; star pattern, close to NN155C; venation is faintly visible, close to 145B; colors do not change with development. Petal, fully opened, lower surface: Main color, close to N80B; star pattern, close to 157D; venation is faintly visible, similar to lamina colors; colors do not change with development. Throat: Distally, close to 157D; center, close to 150D; proximally, close to 145D; venation is faintly visible, close to 145B. Tube:

Distally, close to 157D; proximally, close to 145D; venation is faintly visible, similar to lamina colors.

*Calyx*.—Arrangement: One star-shaped calyx tube with five sepals arranged in a single whorl and fused at the base. Sepal length: About 1 cm. Sepal width: About 2.7 mm. Sepal shape: Lanceolate. Sepal apex: Acute. Sepal margin: Entire. Sepal texture, upper and lower surfaces: Pubescent. Color, upper surface: Close to 137B. Color, lower surface: Close to 137C.

*Peduncles*.—Length: About 2 cm. Diameter: About 1 mm. Strength: Strong, flexible. Aspect: Upright to outwardly. Texture: Pubescent. Color: Close to 144C.

*Reproductive organs*.—Stamens: Quantity per flower: Five. Filament length: About 2 cm. Filament color: Close to NN155B. Anther shape: Ellipsoidal. Anther size: About 2 mm by 1.2 mm. Anther color: Close to NN155A. Pollen amount: Moderate. Pollen color: Close to NN155A. Pistils: Quantity per flower: One. Pistil length: About 2.3 cm. Style color: Close to 145C. Stigma shape: Transversely ellipsoidal. Stigma color: Close to 144A. Ovary color: Close to 144A. Seeds and fruits: Seed and fruit development have not been observed on plants of the new *Petunia* to date.

Garden performance: Plants of the new *Petunia* have been observed to have good garden performance and to tolerate rain, wind and temperatures ranging from about 5° C. to about 35° C.

Pathogen & pest resistance: Plants of the new *Petunia* have not been observed to be resistant to pathogens and pests common to *Petunia* plants to date.

It is claimed:

1. A new and distinct *Petunia* plant named 'Sunpetu 211' as illustrated and described.

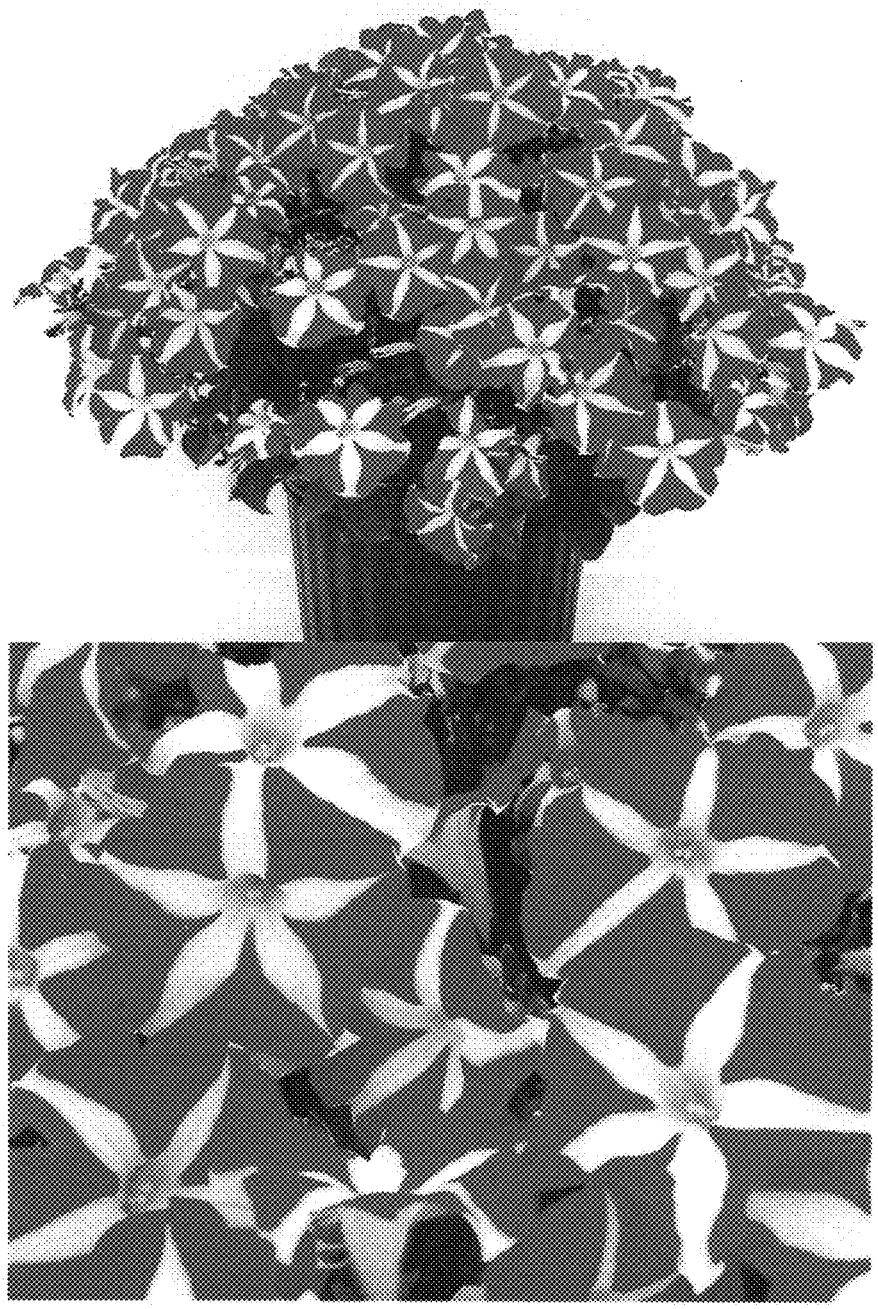

* * * * *